US012774447B2

(12) United States Patent
Lee et al.

(10) Patent No.: US 12,774,447 B2
(45) Date of Patent: Oct. 27, 2026

(54) *BIFIDOBACTERIUM BREVE* JKL2022 STRAIN AND METHOD FOR PRODUCING CONJUGATED LINOLEIC ACID USING THEREOF

(71) Applicant: CHUNG ANG UNIVERSITY INDUSTRY ACADEMIC COOPERATION FOUNDATION, Seoul (KR)

(72) Inventors: Byong Hoon Lee, Toronto (CA); Mun Yhung Jung, Samnye-eup (KR); Geun-Bae Kim, Anseong-si (KR); Arxel G. Elnar, Anseong-si (KR)

(73) Assignee: CHUNG ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 18/879,356

(22) PCT Filed: Jun. 29, 2023

(86) PCT No.: PCT/KR2023/009152

§ 371 (c)(1),
(2) Date: Dec. 27, 2024

(87) PCT Pub. No.: WO2024/005573

PCT Pub. Date: Jan. 4, 2024

(65) Prior Publication Data

US 2026/0002117 A1 Jan. 1, 2026

(30) Foreign Application Priority Data

Jun. 29, 2022 (KR) ........................ 10-2022-0079867

(51) Int. Cl.
*C12N 1/205* (2026.01)
*A23K 10/18* (2016.01)
*A61K 35/00* (2006.01)
*C12P 7/6431* (2022.01)
*C12R 1/00* (2006.01)

(52) U.S. Cl.
CPC .............. *C12N 1/205* (2021.05); *A23K 10/18* (2016.05); *C12P 7/6431* (2022.01); *A61K 2035/115* (2013.01); *C12R 2001/00* (2021.05)

(58) Field of Classification Search
None
See application file for complete search history.

(56) References Cited

FOREIGN PATENT DOCUMENTS

KR 10-2001-0047292 6/2001
KR 10-2010-0128168 A 12/2010
KR 10-2010-0135612 A 12/2010
KR 10-2014-0006509 A 1/2014
KR 10-2016-0100662 A 8/2016
KR 10-1655855 B1 9/2016
KR 10-2017-0078367 A 7/2017
KR 10-2454496 B1 10/2022

OTHER PUBLICATIONS

Fanning et al (Gut Microbes 3(5):420-425, 2012).*
Kiu et al (iScience, 23:101336 Jul. 2020; pp. 1-11 and supplemental).*
Coakley et al (Journal of Applied Microbiology 94:138-145, 2003).*
O'Connell et al (Bioengineered 4(5):313-321, 2013).*
Blankson et al., "Conjugated linoleic acid reduces body fat mass in overweight and obese humans," J Nutr. 130.12: 2943-2948, Dec. 2000.
Fujita et al., "Dietary cis-9, trans-11-conjugated linoleic acid reduces amyloid β-protein accumulation and upregulates anti-inflammatory cytokines in an Alzheimer's disease mouse model," Scientific Reports 11: 9749, 2021 (13 pages).
Hayek et al., "Dietary conjugated linoleic acid influences the immune response of young and old C57BL/6NCrlBR mice," The Journal of Nutrition 129.1: 32-38, 1999.
International Search Report and Written Opinion issued in International Application No. PCT/KR2023/009152 issued by the Korean Intellectual Property Office on Oct. 4, 2023 (9 pages).
Ip et al., "Induction of apoptosis by conjugated linoleic acid in cultured mammary tumor cells and premalignant lesions of the rat mammary gland," Cancer Epidemiol Biomarkers Prev. 9.7: 689-696, Jul. 2000.
Nicolosi et al., "Dietary conjugated linoleic acid reduces plasma lipoproteins and early aortic atherosclerosis in hypercholesterolemic hamsters," Artery 22.5: 266-277, 1997, Abstract only.
Visonneau et al., "Conjugated linoleic acid suppresses the growth of human breast adenocarcinoma cells in SCID mice," Anticancer Res. 17.2A: 969-973, 1997, Abstract only.

(Continued)

*Primary Examiner* — Patricia Duffy
(74) *Attorney, Agent, or Firm* — Klarquist Sparkman, LLP

(57) ABSTRACT

The present invention relates to a *Bifidobacterium breve* JKL2022 strain capable of mass-producing natural conjugated linoleic acid (CLA), and a method for mass-producing conjugated linoleic acid using the same. The method of the present invention makes it possible to easily produce natural CLA in large quantities and high purity of functional CLA in a linoleic acid solution (50 mg/ml) using bacterial cells or cell-free extracts. The cell or cell-free extract of *Bifidobacterium breve* JKL2022 strain of the present invention, and the conjugated linoleic acid (CLA) produced thereby can be widely used in probiotic compositions, pharmaceutical compositions, health functional food compositions, feed additive compositions, and food additive compositions.

6 Claims, 7 Drawing Sheets

Specification includes a Sequence Listing.

(56) References Cited

OTHER PUBLICATIONS

West et al., "Effects of conjugated linoleic acid on body fat and energy metabolism in the mouse," Am J Physiol. 275.3: R667-672, 1998.

* cited by examiner

FIG. 4
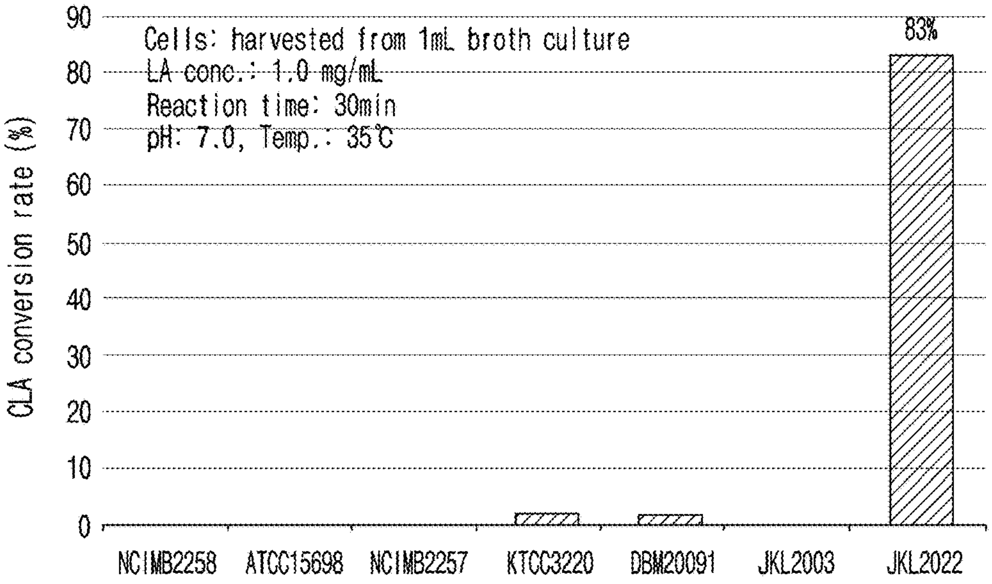
FIG. 5A
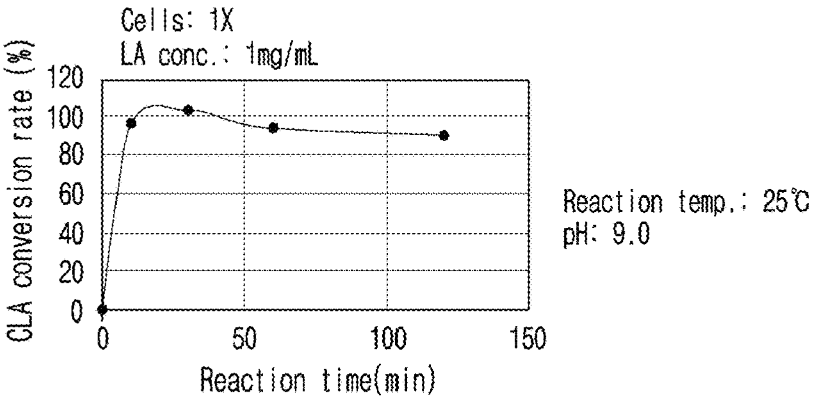
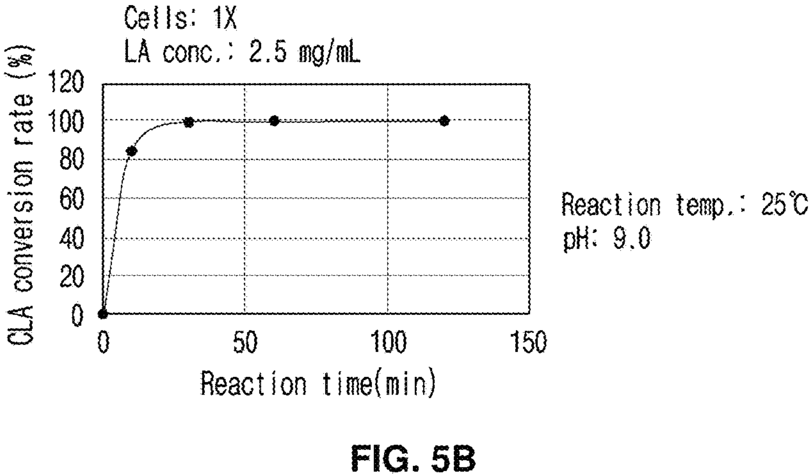
FIG. 5B

FIG. 5C
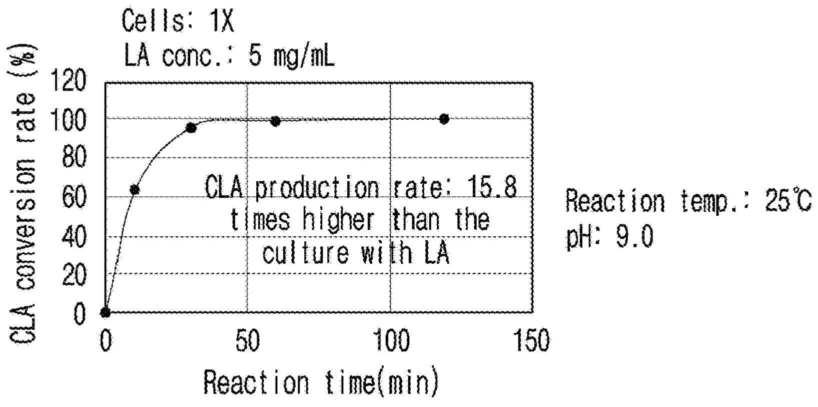
FIG. 5D
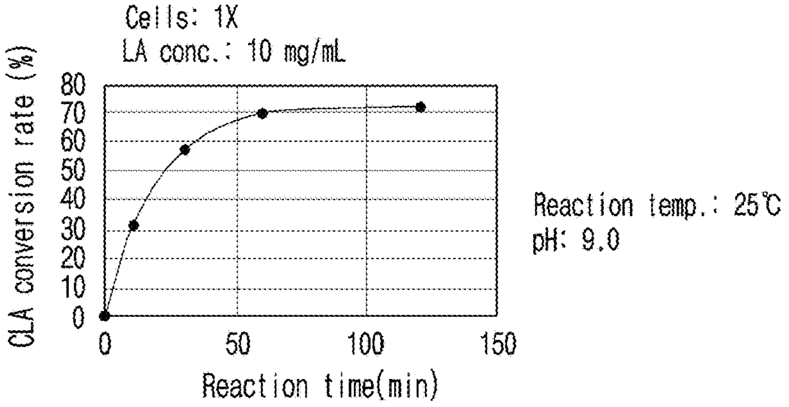
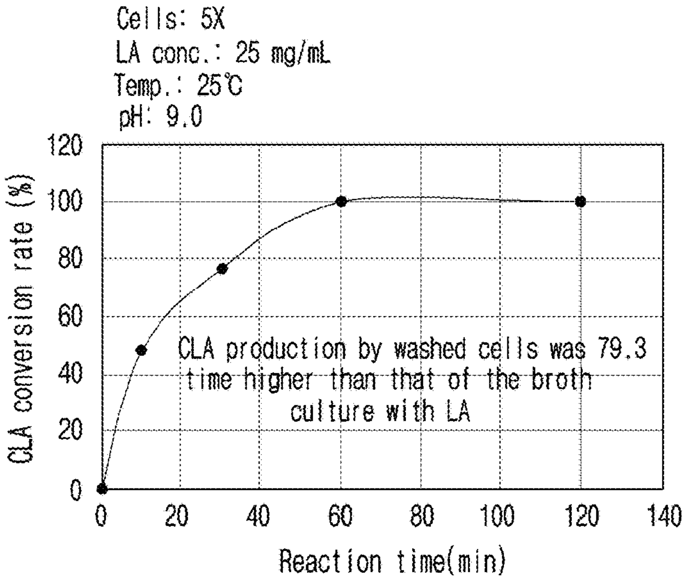
FIG. 6

SEQUENCE LISTING

```
Sequence total quantity: 1
SEQ ID NO: 1            moltype = RNA  length = 1453
FEATURE                 Location/Qualifiers
source                  1..1453
                        mol_type = rRNA
                        organism = Bifidobacterium breve
SEQUENCE: 1
gatgaacgct ggcggcgtgc ttaacacatg caagtcgaac gggatccatc gggctttgcc  60
tggtggtgag agtggcgaac gggtgagtaa tgcgtgaccg acctgcccca tgcaccggaa  120
tagctcctgg aaacgggtgg taatgccgga tgctccatca caccgcatgg tgtgttggga  180
aagcctttgc ggcatgggat ggggtcgcgt cctatcagct tgatggcggg gtaacggccc  240
accatggctt cgacgggtag ccggcctgag agggcgaccg gccacattgg gactgagata  300
cggcccagac tcctacggga ggcagcagtg gggaatattg cacaatgggc gcaagcctga  360
tgcagcgacg ccgcgtgagg gatggaggcc ttcgggttgt aaacctcttt tgttagggag  420
caaggcactt tgtgttgagt gtacctttcg aataagcacc ggctaactac gtgccagcag  480
ccgcggtaat acgtagggtg caagcgttat ccggaattat tgggcgtaaa gggctcgtag  540
gcggttcgtc gcgtccggtg tgaaagtcca tcgcttaacg gtggatccgc gccgggtacg  600
ggcgggcttg agtgcggtag gggagactgg aattcccggt gtaacggtgg aatgtgtaga  660
tatcgggaag aacaccaatg gcgaaggcag gtctctgggc cgttactgac gctgaggagc  720
gaaagcgtgg ggagcgaaca ggattagata ccctggtagt ccacgccgta aacggtggat  780
gctggatgtg gggcccgttc cacgggttcc gtgtcggagc taacgcgtta agcatcccgc  840
ctggggagta cggccgcaag gctaaaactc aaagaaattg acgggggccc gcacaagcgg  900
cggagcatgc ggattaattc gatgcaacgc gaagaacctt acctgggctt gacatgttcc  960
cgacgatccc agagatgggg tttcccttcg gggcgggttc acaggtggtg catggtcgtc  1020
gtcagctcgt gtcgtgagat gttgggttaa gtcccgcaac gagcgcaacc ctcgccccgt  1080
gttgccagcg gattatgccg ggaactcacg gggaccgcc ggggttaact cggaggaagg  1140
tggggatgac gtcagatcat catgcccctt acgtccaggg cttcacgcat gctacaatgg  1200
ccggtacaac gggatgcgac agcgcgagct ggagcggatc cctgaaaacc ggtctcagtt  1260
cggatcgcag tctgcaactc gactgcgtga aggcggagtc gctagtaatc gcgaatcagc  1320
aacgtcgcgg tgaatgcgtt cccgggcctt gtacacaccg cccgtcaagt catgaaagtg  1380
ggcagcaccc gaagccggtg gcctaacccc ttgcgggagg gagccgtcta aggtgaggct  1440
cgtgattggg act                                                     1453
```

*BIFIDOBACTERIUM BREVE* JKL2022 STRAIN AND METHOD FOR PRODUCING CONJUGATED LINOLEIC ACID USING THEREOF

CROSS REFERENCE TO RELATED APPLICATIONS

This is the U.S. National Stage of International Application No. PCT/KR2023/009152, filed Jun. 29, 2023, which in turn claims the benefit of Korean Patent Application No. 10-2022-0079867, filed Jun. 29, 2022. The Korean application is incorporated herein in its entirety.

SEQUENCE LISTING

The nucleic and amino acid sequences listed in the accompanying sequence listing are shown using standard letter abbreviations for nucleotide bases, and single letter code for amino acids, as defined in 37 C.F.R. 1.822. Only one strand of each nucleic acid sequence is shown, but the complementary strand is understood as included by any reference to the displayed strand. The Sequence Listing is submitted as an XML file in the form of the file name "7037-113283-01_Sequence.xml" (~4,096 bytes), which was created on Dec. 26, 2024, which is incorporated by reference herein.

TECHNICAL FIELD

The present invention relates to a method for mass-producing natural conjugated linoleic acid in high purity using *Bifidobacterium breve* JKL2022 strain by whole cells or cell-free extracts.

BACKGROUND ART

CLA (conjugated linoleic acid) is a conjugated isomer of linoleic acid (hereinafter referred to as 'LA'), an essential fatty acid, and is a natural fatty acid component found in trace amounts in the milk or muscles of ruminants. CLA has conjugated double bonds at cis-9 and trans-11 or trans-10 and cis-12 sites in the chain. In particular, it exhibits useful physiological activity in the human body due to the conjugated double bond at cis-9 and trans-11 sites.

CLA was discovered by a research team at the University of Wisconsin in 1987 and has been known to have effects such as reduction of arteriosclerosis, improvement of immune function, anticancer activity, growth promotion, and excellent therapeutic effects on diseases such as diabetes, and suppress obesity through body fat reduction. CLA is a world-class functional substance whose safety has been verified by the U.S. FDA, and it is also a functional substance that has been individually recognized by the Ministry of Food and Drug Safety in Korea.

Due to these characteristics, CLA can be effectively used as an active ingredient in functional foods and medicines. Natural CLA has not yet been produced, and the current global market size of chemically synthesized CLA is USD 50 million (2022) and is expected to be USD 71 million in 2028, with a growth rate of 6.0%. The main companies producing synthetic CLA are BASF, Eastman, Quingdao Aohai and INNOBIO.

CLA is mainly contained in animal foods and is known to be particularly abundant in ruminants. It has been confirmed that the CLA content in beef is 2.9 to 4.3 mg CLA/fat, the CLA content in lamb is 5.6 mg CLA/fat, and the CLA content in seafood is 0.3 to 0.6 mg CLA/fat. The daily intake of CLA in humans is estimated to be 0.1 g/day for Asians who mainly eat vegetables and 0.4 g/day for Westerners who eat a lot of meat. The Korean Food and Drug Administration (KFDA) regulates the CLA standard as a functional ingredient as the sum of cis-9 and trans-11 (c-9, t-11), trans-10 and cis-12 (t-10, c-12), cis-9 and cis-11 (c-9, c-11), and trans-9 and trans-11 (t-9, t-11) (660~850 mg/g). The KFDA also stipulates that the ratio of each ingredient must be such that the sum of the content of cis-9 and trans-11 and trans-10 and cis-12 is at least 90% of the CLA content, and the content of trans-9 and trans-11 is 3% or less.

Despite the well-known high functionality of CLA, the biggest problem in its use is that it exists very little in the natural world. To date, small amounts of cis-9 and trans-11 have been found in ruminant milk, but only very low levels of cis-9 and trans-11 have been detected in fermented dairy products using skim milk. Especially, it is known that cis-9 and trans-11 do not exist even in fermented foods using various lactic acid bacteria.

Until now, several methods have been developed for mass production of CLA. The first method is to chemically synthesize CLA from LA. Most CLA is synthesized through organic synthesis such as alkali-isomerization using LA or LA-rich natural oil used as a raw material, and high-purity CLA is obtained through urea inclusion crystallization. However, chemical synthesis methods have many problems, such as requiring expensive equipment, potential toxicity due to residual organic solvents, and time-consuming processes.

In addition, it is impossible to make a single type of CLA because various types of isomers are simultaneously produced through conventional chemical methods. Since the in vivo safety of some isomers has not been confirmed and some have been reported to be toxic, it is a very difficult process to produce only the functional type of CLA isomers.

The second method is to use microorganisms with activity that can convert LA into CLA. Various types of bacteria (*Lactobacillus, Bifidobacterium, Propionibacterium, Clostridium, Butyrivibrio*, etc.) have been reported to have the ability to convert LA to CLA, and few microorganisms with activity that can convert LA to CLA have been isolated. Representative microorganisms known to produce CLA are intestinal microorganisms such as *Bifidobacterium, Lactobacillus, Propionibacterium*, and *Butyrivibrio fibrisolvens*, which are usefully used as active ingredients in functional foods or medicines such as probiotics and feeds administered to livestock in many countries.

Among them, *Bifidobacterium breve* strains are known to show the highest conversion rates, and this characteristic has been reported to exhibit strain-specificity. The method of producing natural CLA using microorganisms is the best method, but the strains reported so far have not yet been commercialized due to their low yields.

The concentration of LA, which can be added as a substrate to the medium to produce CLA through the microbial culture process, is about 0.5 mg/ml, which is the upper limit due to the antiproliferative effect of LA on bacteria, so the yield is very low. Therefore, there is a limit in mass production.

Prior arts for producing and isolating CLA from microorganisms capable of producing CLA include the following: Korean Patent Publication No. 2001-0047292 relates to a strain producing conjugated linoleic acid (CLA) and discloses a *Bifidobacterium longum* CGB-C11 (accession number: KCTC 11979BP) strain, and Korean Patent Publication No. 2014-0006509 discloses a *Lactobacillus gasseri* CBGC20 strain that produces conjugated linoleic acid (CLA).

The inventors of the present invention have isolated a novel *Bifidobacterium breve* JKL2022 strain from the fresh feces of Korean newborn infants. This *B. breve* JKL2022 strain not only can treat various diseases as a functional probiotic preparation, but also can convert almost all of LA into CLA when using its cell or cell-free extract (crude enzyme solution). The strain also has a higher CLA production rate than existing comparative strains and CLA's highly functional isomers, c9, t11-CLA, are selectively mass-produced with very high purity of 98% or more.

DISCLOSURE OF INVENTION

Technical Problem

The purpose of the present invention is to provide a method for mass production of highly pure conjugated linoleic acid using a whole cell or cell-free extract of *Bifidobacterium breve* JKL2022 (hereinafter referred to as 'JKL2022') isolated from the intestines of a healthy human body.

Solution to Problem

To achieve the above objective, the present invention provides a novel *Bifidobacterium breve* JKL2022 strain isolated from infant feces, its whole cell or cell-free extract.

The present invention also provides a method for producing CLA using a novel *Bifidobacterium breve* JKL2022 strain.

The present invention also provides a pharmaceutical composition comprising a novel *Bifidobacterium breve* JKL2022 strain, its cell or cell-free extract as an active ingredient.

The present invention also provides a health functional food composition comprising a novel *Bifidobacterium breve* JKL2022 strain, its cell or cell-free extract as an active ingredient.

The present invention also provides a probiotic strain comprising a novel *Bifidobacterium breve* JKL2022 strain, its cell or cell-free extract as an active ingredient.

The present invention also provides an animal feed composition comprising a novel *Bifidobacterium breve* JKL2022 strain, its cell or cell-free extract as an active ingredient.

In addition, the present invention provides a food comprising a novel *Bifidobacterium breve* JKL2022 strain, its cell or cell-free extract as an active ingredient.

Advantageous Effects of Invention

The cell or cell-free extract of *Bifidobacterium breve* JKL2022 strain of the present invention has the effect of selectively mass-producing c9/t11-CLA (with a purity of 98% or more), which is a highly functional isomer of CLA, by reacting with linoleic acid used as a substrate. The cell or cell-free extract of *Bifidobacterium breve* JKL2022 strain of the present invention, and the conjugated linoleic acid (CLA) produced thereby can be widely used in probiotic compositions, pharmaceutical compositions, health functional food compositions, feed additive compositions, and food additive compositions.

BRIEF DESCRIPTION OF DRAWINGS

FIG. 4 is a graph showing the results of comparing the CLA production capacity of *Bifidobacterium breve* JKL2022 strain cells with other strains according to the present invention.

FIGS. 5A-5D are a set of graphs showing the results of confirming the CLA production and conversion rate by *Bifidobacterium breve* JKL2022 strain cells according to the present invention by the concentration of added LA. (A) LA conc.: 1.0 mg/mL; (B) LA conc.: 2.5 mg/mL; (C) LA conc.: 5.0 mg/mL; (D) LA conc.: 10 mg/mL.

FIG. 6 is a graph showing the results of increasing the concentration of cells and the concentration of LA, a substrate, to optimize the CLA production conditions by *Bifidobacterium breve* JKL2022 strain cells according to the present invention.

BEST MODE FOR CARRYING OUT THE INVENTION

Figure 1:
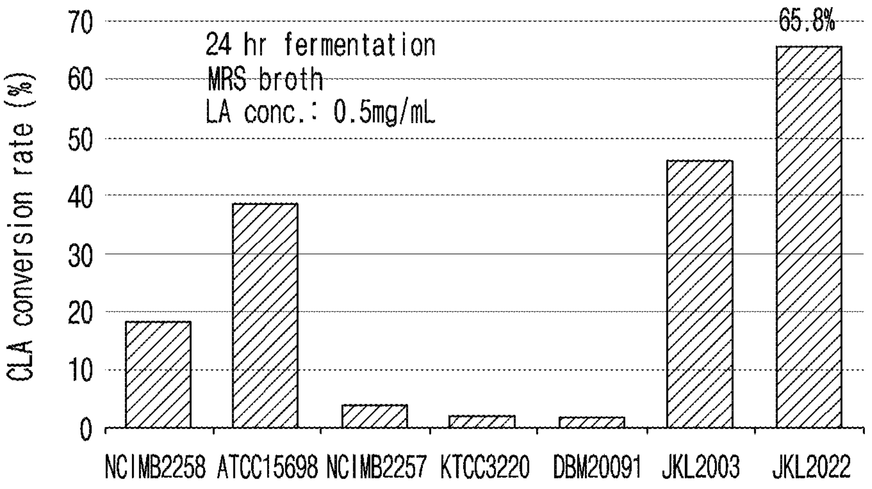
FIG. 1 is a graph showing the results of comparing the amount of CLA produced through the culture process for each strain.

1. To Achieve the Objective of the Present Invention, the Present Invention Provides a Novel *Bifidobacterium breve* JKL2022 Strain (KACC 81214BP).

1-1. Isolation of a Novel *Bifidobacterium breve* JKL2022 Strain

The above strain was isolated from the feces of a healthy Korean infant under breastfeeding. The appropriately diluted fecal samples were plated and cultured to isolate a pure strain.

For the pure strains isolated, the presence of a gene encoding F6PPK (fructose-6-phosphate phosphoketolase) common among *Bifidobacterium* strains was confirmed by PCR (genus-specific PCR), and the strains belonging to the

*Bifidobacterium* genus were first identified. *Bifidobacterium breve* strains were finally isolated and identified by species-specific PCR using a primer set prepared based on 16S rRNA gene sequence information.

The new strain of the present invention has the 16S rRNA gene nucleotide sequence represented by SEQ. ID. NO: 1.

The CLA production capacity of the newly isolated and identified *Bifidobacterium breve* strains was compared with previously reported strains, and the strains with excellent CLA production capacity were selected. Among them, the strain of the present invention had the best CLA production capacity (see FIG. 1).

The genus and species were identified through BLAST search by analyzing the 16S rRNA gene nucleotide sequence. The JKL2022 strain was deposited at Korean Agricultural Culture Collection (KACC), National Institute of Agricultural Sciences (NAS) as *Bifidobacterium breve* JKL2022 (KACC 81214BP) on May 11, 2022.

1-2. CLA Produced by *Bifidobacterium breve* JKL2022 Strain

For the selected strains, the fatty acid produced by each strain was analyzed by GC-FID (Agilent 7890A) to confirm again whether the strain could produce CLA from LA, and an additional confirmation experiment for the CLA isomer produced was conducted using silver ion impregnated HPLC (HPLC, Shimadzu, Tokyo, Japan). In addition, to reconfirm the double bond position of CLA, fatty acids were extracted, and GC-MS analysis was performed with methyl esterified samples.

The content of each fatty acid on the GC chromatogram obtained by performing GC analysis was quantified by comparing the peak areas of heptadecanoic acid (C17:0), an internal standard, with the peak area of each fatty acid (see FIGS. 2A-2D and 3).

From the above experiments, it was confirmed that most of the fatty acid obtained according to the present invention is c9, t11-conjugated linoleic acid.

2. The Present Invention Provides a Method for Producing CLA Using a Novel *Bifidobacterium breve* JKL2022 Strain.

The present invention also provides a method for producing conjugated linoleic acid comprising a step of culturing the strain of the present invention. The strain is preferably a *Bifidobacterium breve* JKL2022 strain (accession number: KACC 81214BP). As a method for culturing the strain of the present invention, a method commonly used in industry can be used.

2-1. A Method Using Cells 1 ml of *Bifidobacterium breve* JKL2022 strain culture product obtained through enrichment culture was centrifuged and washed to obtain a microbial whole cell pellet, and this pellet was suspended in a reaction buffer containing LA at a concentration of 1.0 mg/ml. Then, the conversion rate (%) of LA to CLA under the CLA production conditions (pH: 7.0, reaction temperature: 30° C., reaction time: 30 minutes) using the cells was confirmed (see FIG. 4)

As shown in FIG. 1, when LA was added to the medium in which the strain was cultured continuously, CLA was also produced in small amounts in other strains. However, when the cells obtained by culturing the strain were added and cultured, it was found that CLA was not produced in other strains that showed the ability to produce CLA by culturing the strain (see FIG. 10).

When microbial cells were used as a whole-cell biocatalyst, the production of CLA was confirmed as a characteristic of only *Bifidobacterium breve* JKL2022 strain according to the present invention (see FIG. 4).

As shown in FIGS. 5A-5D, CLA production and conversion rate of the strain according to the concentration of LA while fixing the concentration of the microbial cells and increasing the amount of LA were investigated. It was confirmed that CLA was produced at a conversion rate of almost 100% within 30 minutes even if the concentration of LA in the reaction solution was increased to 5 mg/ml. A conversion rate of 70% (7 mg/ml CLA) was also confirmed at the LA concentration of 10 mg/ml.

As shown in FIG. 6, it was confirmed that almost all LA could be converted to CLA in one hour of reaction even if the concentration of the cells was increased by 5 times and the concentration of LA was 25 mg/ml.

Considering that an upper limit of LA concentration that can be added to the medium is up to 0.5 mg/ml in the production of CLA through the fermentation process of conventional strains, it can be seen as a very remarkable effect.

The production rate of CLA using *Bifidobacterium breve* JKL2022 cells was about 79 times higher than that obtained through the culture process of *Bifidobacterium breve* JKL2022 strain. The fact that the reaction using whole cells takes only 1 hour, while the production of CLA through culture process takes 24 hours, is also a big advantage.

Figure 7:
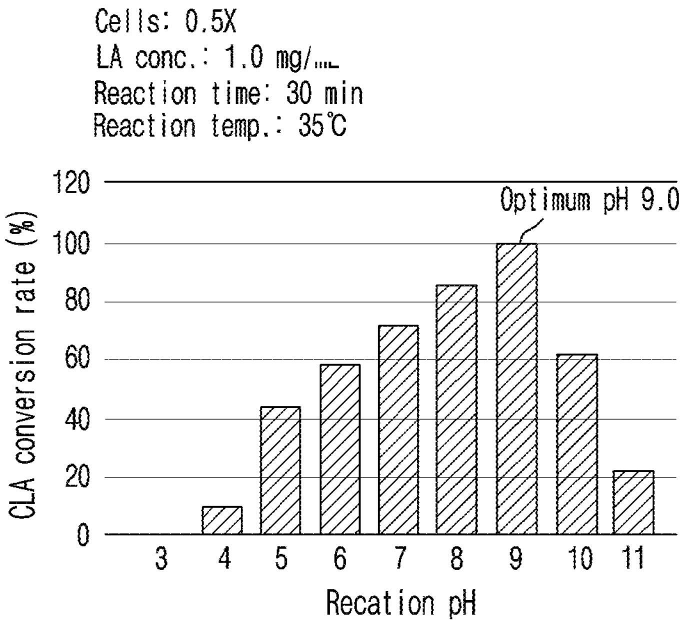
FIG. 7 is a graph showing the results of confirming the optimal pH for the CLA production by *Bifidobacterium breve* JKL2022 strain cells according to the present invention.

As shown in FIG. 7, the pH conditions for CLA production using the whole cells were pH 7-10, preferably pH 9.0.

2-2. A Method Using Cell-Free Extract

After centrifuging the culture product obtained by inoculating the strain activated through subculture in a medium (200 ml), the supernatant, the medium component, was discarded, and the cells at the bottom were recovered and washed.

The washed cells were resuspended in a PBS solution, and the cells were disintegrated by ultrasonication. After centrifugation of the disintegrated cells, the supernatant was recovered to prepare a cell-free extract (CFE) and used as a crude enzyme solution for CLA production.

Figure 8:
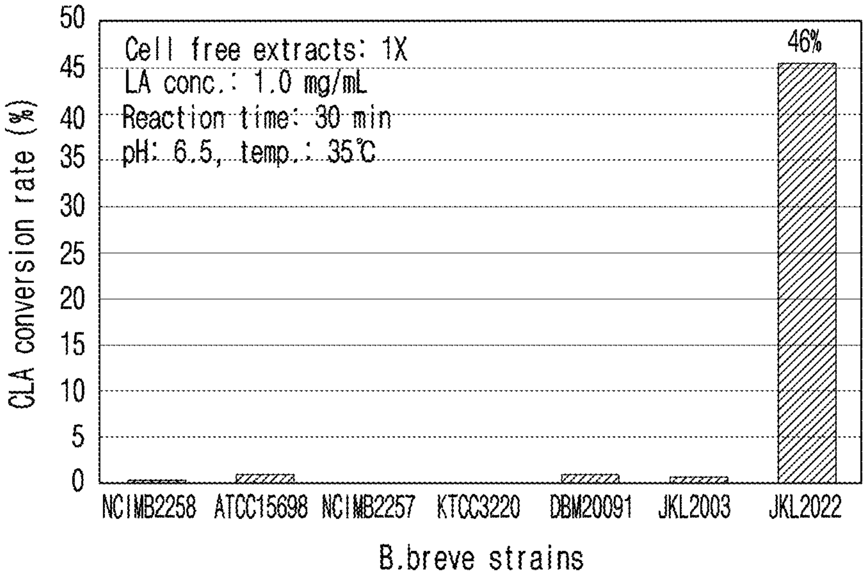
FIG. 8 is a graph showing the results of comparing the CLA production capacity of the cell-free extract prepared by cell disintegration of *Bifidobacterium breve* JKL2022 strain with the other comparative strains according to the present invention.

As shown in FIG. 8, it was found that the CLA production capacity of the cell-free extract of *Bifidobacterium breve* JKL2022 strain according to the present invention was better than those of the comparative strains.

Figure 9:
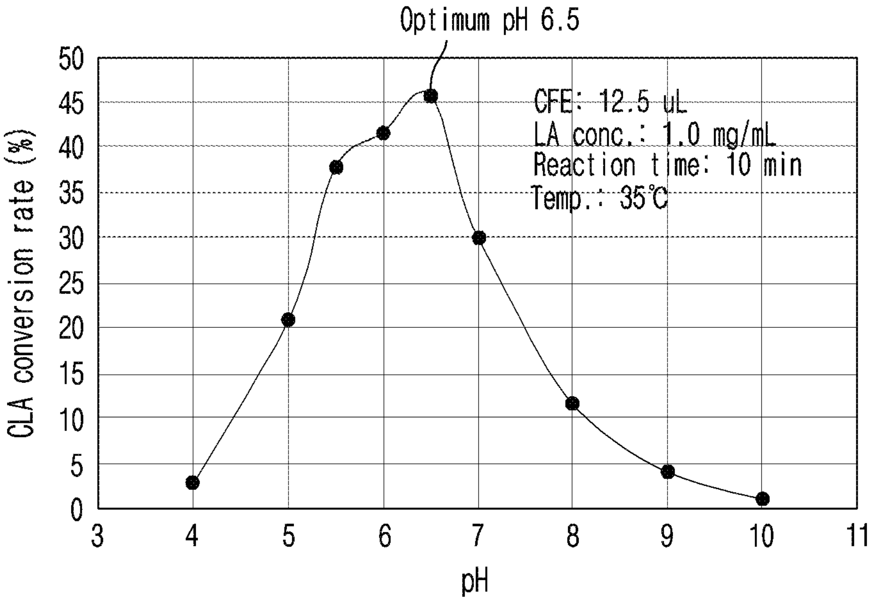
FIG. 9 is a graph showing the results of confirming the optimal pH for the CLA production by the cell-free extract prepared by cell disintegration of *Bifidobacterium breve* JKL2022 strain according to the present invention.

As shown in FIG. 9, the pH conditions for CLA production using the cell-free extract of the strain were pH 5-7.5, preferably pH 5.5-7, and most preferably pH 6.5.

Figure 10:
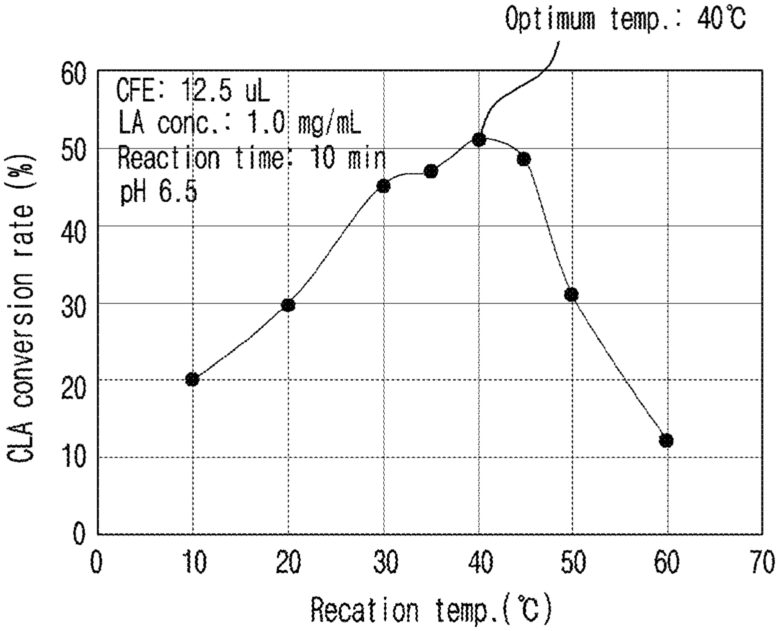
FIG. 10 is a graph showing the results of confirming the optimal temperature for the CLA production by the cell-free extract prepared with cell disintegration of *Bifidobacterium breve* JKL2022 strain according to the present invention.

As shown in FIG. 10, the temperature conditions for CLA production using the cell-free extract of the strain were 20-50° C., preferably 30-45° C., and most preferably 40° C.

3. The Present Invention Provides Probiotic Preparations (Pharmaceutical Composition, Health Functional Food Composition, Food) Comprising a Novel *Bifidobacterium breve* JKL2022 Strain.

The strain (*Bifidobacterium breve* JKL2022) of the present invention produces CLA, and the produced CLA is known to reduce the incidence of arteriosclerosis (Artery. 1997. 22:266-277), improve immune function (J. Nut. 1999. 129:32-38), has anticancer activity (Anticancer research. 1997. 17:969-973), exhibit excellent therapeutic effects on diseases such as diabetes, and suppress obesity by reducing body fat (AM. J. Registered Patent 10-1655855-6—Physiol. 1998. 275: R667-R672). More recently anti-Alzheimer's disease effect by c9, t11 CLA is also reported (Sci. Report. 2011. 11:9749). Therefore, the strain (*Bifidobacterium breve* JKL2022) of the present invention, its cell or cell-free extract can be used as a pharmaceutical composition for improving immune function or for preventing or treating cancer, arteriosclerosis, diabetes, obesity, and Alzheimer disease.

The probiotic preparation of the present invention strain can be applied to all uses known as the functionality of the conventional CLA. Specifically, the probiotic preparation can be applied to pharmaceutical compositions, health functional food compositions, and foods. The food can be specifically applied to cheese, yogurt, milk powder, ice cream, and the like, and most preferably to cheese and yogurt.

The dosage or intake of the pharmaceutical composition of the present invention is preferably 60 to 130 μM (Cancer Epidemiol. Biol. Prev. 2000. 9:689-696), and the dosage or intake of the functional food is preferably 3.4 to 6 g/day (J. Nutr. 2000. 130:2943-2948) but can be increased or decreased as necessary. The pharmaceutical composition of the present invention is safely absorbed into the body regardless of the amount of intake. The dosage or intake can be adjusted according to various factors, including the type and content of active ingredients and other components in the pharmaceutical composition, the type of formulation, the patient's age, weight, general health status, gender and diet, administration time, route and composition secretion rate, treatment period, and drugs used concurrently. When the pharmaceutical composition of the present invention is administered to a human body, there is no concern about side effects compared to the foods and medicines containing chemically synthesized CLA.

The food or pharmaceutical composition of the present invention can include one or more pharmaceutically or sitologically acceptable carriers in addition to an active ingredient selected among the stomach cancer inhibitors, such as saline, sterilized water, Ringer's solution, dextrose solution, maltodextrin solution, glycerol, ethanol, and a mixture comprising one or more of those components. If necessary, other common additives such as antioxidants, buffers, and bacteriostatic agents can be added. The composition of the present invention can be formulated in different forms including aqueous solutions, suspensions and emulsions for injection, pills, capsules, granules, or tablets by mixing with diluents, dispersing agents, surfactants, binders, and lubricants. The composition can further be preferably formulated in suitable forms according to each disease or component by using an appropriate method in the art or by using a method disclosed in Remington's Pharmaceutical Science (the newest edition), Mack Publishing Company, Easton PA.

The formulation form of the pharmaceutical composition of the present invention can be granules, powders, coated tablets, tablets, capsules, decoctions, extracts, suppositories, syrups, juices, suspensions, emulsions, sustained-release formulations of active ingredient, etc.

In addition, the strain of the present invention can be added to food or medicine in the form of live cells as well as dead cells (parabiotics). This is because the strain of the present invention has the characteristics of accumulating a significant amount of CLA in cells while secreting CLA into the culture medium or reaction solution. Accordingly, since CLA can be indirectly produced by adding the cultured strain in the LA-added medium to various compositions such as food and medicine as an active ingredient, it can promote the development of functional products containing large amounts of CLA.

The present invented strain, *Bifidobacterium breve* JKL2022, its cell or cell-free extract can be used as an animal feed composition.

The present invented strain, *Bifidobacterium breve* JKL2022, its cell or cell-free extract can be used as a food additive composition.

MODE FOR THE INVENTION

Hereinafter, the present invention will be described in detail by the following examples. However, the following examples are only for illustrating the present invention, and the contents of the present invention are not limited thereto.

Example 1: Isolation and Identification of Strains of the Present Invention

To isolate the strain of the present invention, the feces of a healthy Korean infant under breastfeeding were collected. To isolate *Bifidobacterium breve* strain known to have high CLA production capacity by previous studies, appropriately diluted fecal samples were plated on a TOS (Trans-galactosylated oligosaccharide) propionate agar medium (Yakult Pharmaceutical, Japan), a *Bifidobacterium* selection medium, after decimal dilution using an anaerobic microbial diluent, cultured anaerobically at 37° C. for 48 hours, and then typical colonies were taken for pure isolation.

For the pure isolated strains, the presence of a gene encoding F6PPK (fructose-6-phosphate phosphoketolase) common among *Bifidobacterium* strains was confirmed by PCR (genus-specific PCR), and the strains belonging to the *Bifidobacterium* genus were first identified. *Bifidobacterium breve* strains were finally isolated and identified by species-specific PCR using a primer set prepared based on 16S rRNA gene sequence information.

The CLA production capacity of the newly isolated and identified *Bifidobacterium breve* strains was compared with previously reported strains, and a strain with excellent CLA production capacity was selected and named as JKL2022. The genus and species were identified through BLAST search by analyzing the nucleotide sequence of the 16S rRNA gene for the strain of the present invention. As a result, JKL2022 was determined to be *Bifidobacterium breve*. As shown in Table 1, the newly isolated strain had a difference of 1 to 5 bases in the 16S rRNA gene nucleotide sequence from the strains previously reported to have high CLA production capacity, so the novelty of the strain was recognized. The JKL2022 strain was deposited at Korean Agricultural Culture Collection (KACC), National Institute of Agricultural Sciences (NAS) as *Bifidobacterium breve* JKL2022 (KACC 81214BP) on May 11, 2022.

TABLE 1

Novel strain identification by comparing 16S rRNA gene sequence

| Strains compared | 16S rRNA gene match rate | Different base number |
|---|---|---|
| *Bifidobacterium breve* KCTC3220$^T$ | 99.93% (1452/1453) | 1 |
| *Bifidobacterium breve* DSM20091 | 99.66% (1448/1453) | 5 |
| *Bifidobacterium breve* NCFB2257 | 99.86% (1451/1453) | 2 |
| *Bifidobacterium breve* NCFB2258 | 99.66% (1448/1453) | 5 |
| *Bifidobacterium breve* ATCC15698 | 99.66% (1448/1453) | 5 |
| *Bifidobacterium breve* LMC520 | 99.86% (1451/1453) | 2 |
| *Bifidobacterium breve* NCTC11815 | 99.86% (1451/1453) | 2 |
| *Bifidobacterium breve* JCM7017 | 99.72% (1450/1453) | 4 |
| *Bifidobacterium breve* JCM7019 | 99.66% (1448/1453) | 5 |
| *Bifidobacterium breve* JCM1273 | 99.66% (1448/1453) | 5 |

Example 2: Comparison of *Bifidobacterium Breve* JKL2022 with Other Strains

<2-1> Comparison of CLA Production Capacity of *Bifidobacterium breve* JKL2022 and Other Strains Through Microbial Culture For the production of CLA, the above strain was inoculated into MRS medium (mMRS; Sigma) containing 0.05% L-cysteine HCl and activated through two rounds of subculture at 37° C. for 18 hours under anaerobic conditions where $O_2$ was replaced with $CO_2$. Then, the strain was inoculated into the new mMRS medium added with linoleic acid (LA), a substrate, at a concentration of 0.5 mg/mL, and cultured at 37° C. for 24 hours under anaerobic conditions to convert LA into CLA.

FIG. 1 is a graph showing the results of comparing the CLA conversion rate of *Bifidobacterium breve* JKL2022 strain according to the present invention with other *Bifidobacterium breve* strains. It has been reported that the amount of CLA produced by the prior art through the culture process of microorganisms increases with the growth of the strain. The amount of CLA produced by culture of *Bifidobacterium breve* JKL2022 strain according to the present invention was confirmed to be 0.33 mg/ml (conversion rate: 65.8%). Comparing the CLA production ability through *Bifidobacterium* cultures, the production was highest when using *Bifidobacterium breve* JKL2022 strain of the present invention (FIG. 1).

Example 3: Confirmation of c9, t11-CLA Isomers Through Structural Analysis of Produced CLA <3-1> Pretreatment for Fatty Acid Analysis of Reactants (Methylation)

1N NaOH or 1N HCl was added dropwise to 4 mL of the reactant to adjust the pH to 7.0, and 0.1 mL of an internal standard (C17:0; 10 mg/mL hexane) and 4 mL of an extraction solvent (hexane) were added thereto, mixed with 2 mL of saturated NaCl aqueous solution, shaken sufficiently, and allowed to stand for 30 minutes. Then, the sample was centrifuged (1,900×g, 5 minutes) and the separated hexane layer was transferred to a new glass tube. The extract obtained after additionally extracting using 4 mL of extraction solvent (hexane) was transferred to the same glass tube, and nitrogen concentration was performed at 45° C. When the solvent was completely removed, 1 mL of 1.0% HCl in methanol was added and reacted at 60° C. for 30 minutes to perform fatty acid methylation. Upon completion of the reaction, a supernatant was obtained by extracting fatty acid methyl esters by adding 2 mL of saturated NaCl solution and 1 mL of hexane. To the supernatant obtained, a small amount of anhydrous sodium sulfate was added to remove moisture and transferred to a vial for GC analysis.

<3-2> Fatty Acid Identification and Quantification Experiments

1) GC/FID (Gas Chromatography/Flame Ionization Detector)

The fatty acid methyl ester obtained by the above method was analyzed by GC-FID (Agilent 7890A). At this time, Supelcowax-10 fused silica capillary column (100 m×0.32 mm i.d., 0.25 μm film thickness) was used as a column. Helium used as a moving phase was supplied at a rate of 1.2 mL/min. The temperature of the sample injector and detector was 260° C., and the temperature of the oven was raised from 190° C. to 240° C. at a rate of 4° C. per minute and then maintained. The fatty acid of each peak was first confirmed through the retention time of each fatty acid standard.

2) Silver Ion Impregnated HPLC

Further confirmation of the generated CLA isomers was performed using silver ion impregnated HPLC (HPLC, Shimadzu, Tokyo, Japan). The generated CLA was methyl esterified by the above method, and then three silver ion impregnated columns (ChromSpher 5 Lipids analytical silver-impregnated column, 4.6 mm i.d.×250 mm stainless steel, 5 μm particle size; Chrompack, Bridgewater, NJ, USA) were connected in series and used. As a moving phase, 0.1% acetonitrile in hexane was flowed at a rate of 1.0 mL/minute to perform analysis. To confirm the CLA isomer, the retention time was compared by analyzing the standard CLA isomer mixtures under the same conditions. In addition, the CLA isomer was further confirmed by performing silver ion impregnation HPLC using a method of simultaneously injecting a mixture of the standard and the CLA produced by the method of the present invention.

3) GC-MS (Gas Chromatography/Mass Spectrometry)

To reconfirm the location of the double bond of CLA, GC-MS was performed after 4,4-dimethyloxazoline (DMOX) derivatives of fatty acid methyl ester (FAMEs) were prepared. After methyl esterification of CLA produced by JKL2022 cells, DMOX derivatization reaction was performed again. About 10 mg of methyl esterified (FAMES) CLA was added to a test tube, and then 50 mg of 2-amino-2-methyl-1-propanol, a derivatization reagent, was added thereto. Thereafter, after purging with argon gas, the lid was tightly closed, and the reaction was carried out at 170° C. for 6 hours. After cooling to room temperature, diethyl ether/hexane (1:1, vol/vol; 5 mL) and distilled water (5 mL) were added to the test tube, shaken, and allowed to stand, and the obtained supernatant (diethyl ether/hexane) was recovered. A small amount of anhydrous sodium sulfate was added to the recovered supernatant to remove water, and the solvent was removed using nitrogen. 0.5 mL of the DMOX derivatives of fatty acids obtained was re-dissolved in 2,2,4-trimethylpentane, and GC-MS analysis was performed.

The DMOX derivatives of fatty acid methyl ester prepared by the above method were analyzed using gas chromatography-mass spectrometry (a Perkin-Elmer Auto System XL). At this time, a Supelcowax-10 fused silica capillary column (100 m×0.32 mm i.d., 0.25 μm film thickness) was used as a column. Helium used as a moving phase was supplied at a rate of 1.2 mL/min. The temperature of the sample injector and detector was 260° C., and the temperature of the oven was raised from 190° C. to 240° C. at a rate of 4° C. per minute and then maintained. The inlet, transfer line, and ion source temperatures were 260, 220, and 260° C., respectively, and the sample was ionized at 70 eV using the EI ionization mode.

4) Analysis of Fatty Acid Content Using GC-FID

GC analysis was performed on the sample obtained by extracting fatty acids and methyl esterified fatty acids under the above conditions of GC-FID. The content of each fatty acid obtained from GC chromatogram was quantified by comparing the peak area of the internal standard heptadecanoic acid (C17:0) and the peak area of each fatty acid.

Figure 2A:
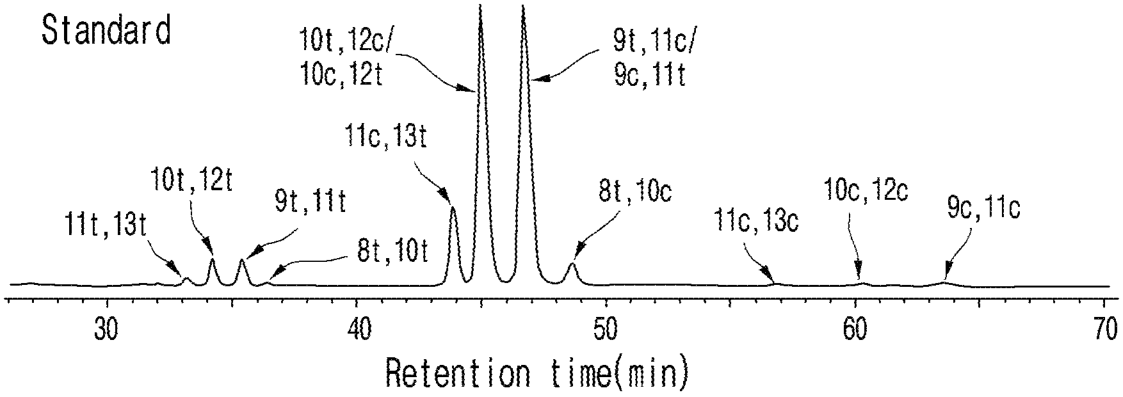
FIG. 2A is a graph showing the results of confirming the CLA isomers of the CLA standard mixture using GC/FID and Silver ion impregnated HPLC.
Figure 2B:
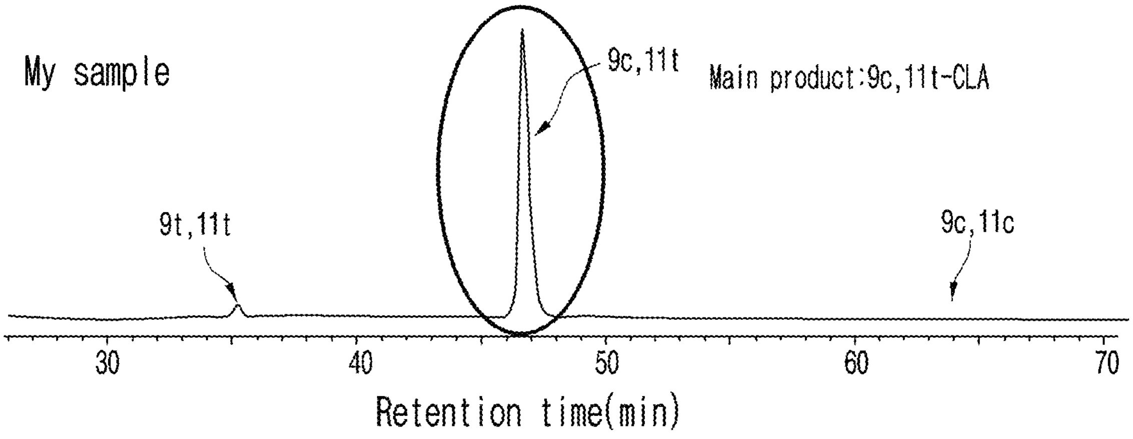
FIG. 2B is a graph showing the results of confirming the CLA isomers of the sample produced by *Bifidobacterium breve* JKL2022 strain according to the present invention using GC/FID and Silver ion impregnated HPLC.
Figure 2C:
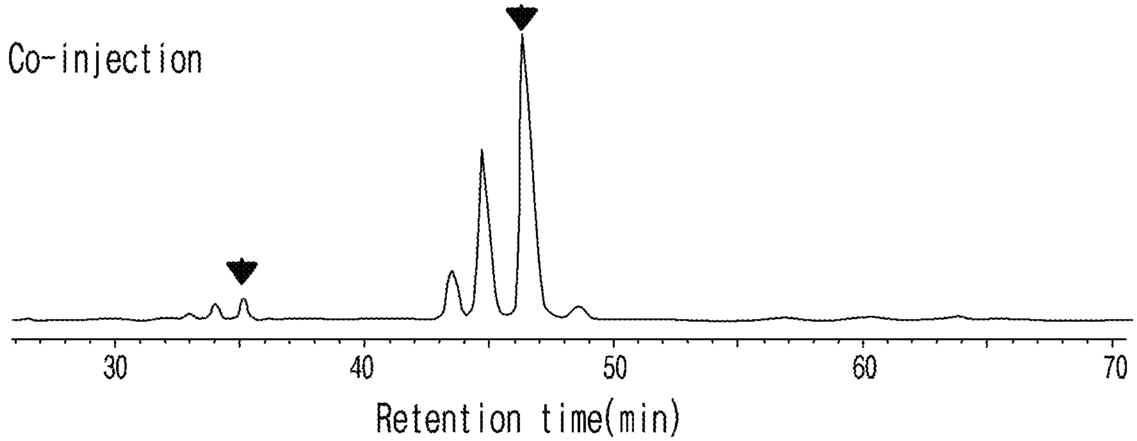
FIG. 2C is a graph showing the results of confirming the CLA isomers produced using a method of co-injection after mixing the CLA produced by *Bifidobacterium breve* JKL2022 strain with a standard product.
Figure 2D:
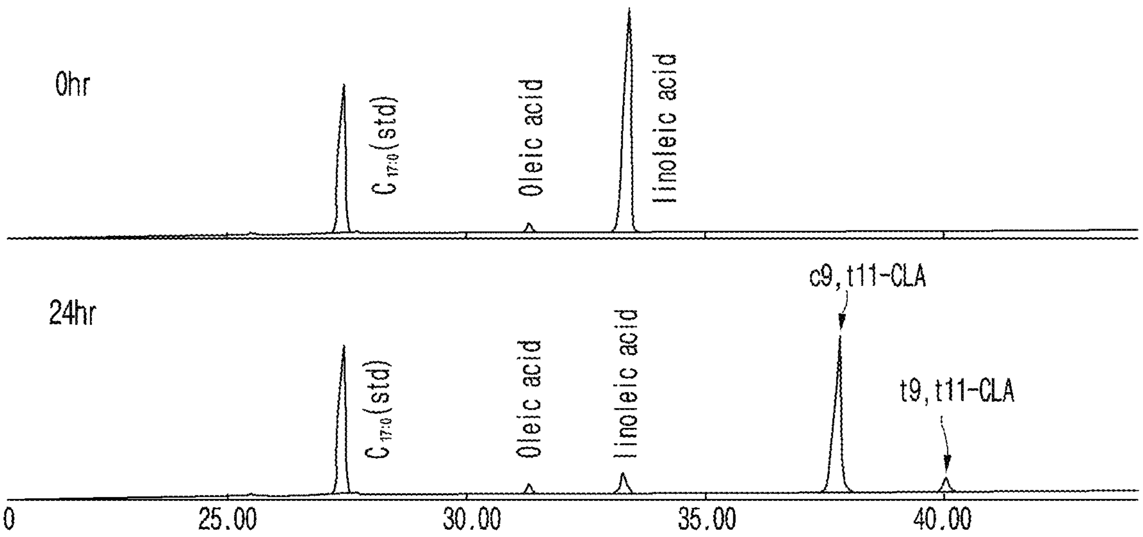
FIG. 2D is a set of graphs showing the results of confirming that LA was converted to isomeric CLA by culturing *Bifidobacterium breve* JKL2022 strain for 24 hours according to the present invention.

As shown in FIG. 2D, it was confirmed that linoleic acid was converted into a completely new fatty acid in MRS broth using *Bifidobacterium breve* strain JKL2022. To confirm the type of fatty acid produced, the CLA standard mixture was analyzed by GC under the same conditions and compared with the standard retention time. It was primarily confirmed that the produced fatty acids were c9/t11 CLA isomers, along with trace amounts of c9/c11, and t9/t11. In addition, the structure of these fatty acids was compared and reconfirmed by comparative analysis with a standard CLA mixture whose structure is known using silver ion impregnated HPLC. In particular, an additional experiment was conducted by co-injecting a mixture of the CLA produced by *Bifidobacterium breve* JKL2022 strain and the standard products. As a result, it was further confirmed that the major isomers were c9/t11-CLA with trace amounts of c9/c11 and t9/t11-CLA isomers.

Figure 3:
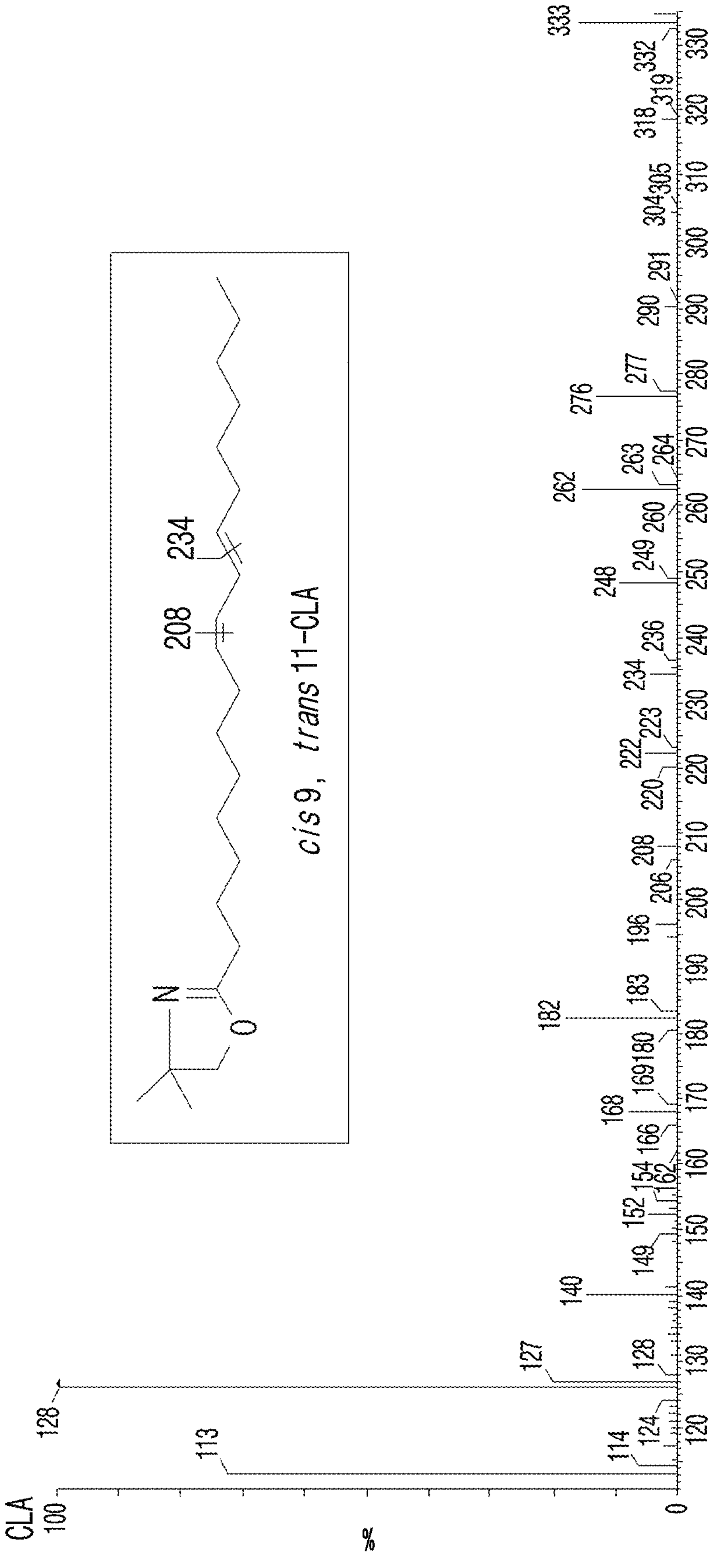
FIG. 3 is a graph showing the structure of the CLA isomers produced by *Bifidobacterium breve* JKL2022 strain using GC-MS according to the present invention.

FIG. 3 shows a mass chromatogram obtained by preparing a DMOX derivatives of fatty acids and analyzing thereof by GC-MS to confirm the number and position of double bonds located in the fatty acid of the CLA produced by *Bifidobacterium breve* JKL2022 strain. From this chromatogram, the molecular ion value was confirmed as m/z 333, indicating that it had a fatty acid structure with 18 carbon atoms and two double bonds. In addition, it was confirmed that the mass ion values were m/z 208 and m/z 234, and the position of the double bond was the 9th carbon and the 11th carbon, thereby confirming the structure of the conjugated state. Therefore, it was confirmed that the fatty acid obtained by this experiment was c9/t11-conjugated linoleic acid.

Example 4: Optimal CLA Production Using *Bifidobacterium breve* JKL2022 Cells (Live Cells)

In this example, *Bifidobacterium breve* JKL2022 strain (KACC 81214BP) having the highest CLA production activity among various *Bifidobacterium* strains was used.

For the production of CLA, the above strain was inoculated into MRS medium (mMRS; Sigma) containing 0.05% L-cysteine HCl and activated through two rounds of subculture at 37° C. for 18 hours under anaerobic conditions where $O_2$ was replaced with $CO_2$.

The activated strain was inoculated into new mMRS medium (200 ml) and cultured at 37° C. for 24 hours under anaerobic conditions to obtain a strain. The culture solution of the strain was centrifuged at 10,000 rpm for 10 minutes at 4° C. The supernatant, which is a medium component, was discarded and recovered the cells collected and washed with PBS (phosphate buffered saline) that was repeated three times. Then, the cells were resuspended again in PBS solution (10 ml), concentrated 20 times, and stored at 4° C. and used as a whole-cell biocatalyst for CLA production. The cells prepared for CLA production using cells were used at the same concentration (1×) as when growing in the enrichment medium, and various concentrations of LA were mixed with a reaction buffer to confirm the CLA production efficiency according to the reaction time, reaction temperature, and pH of the reaction solution.

<4-1> CLA Conversion Rate Using Bacteria Whole Cells of the Strain of the Present Invention A whole cell pellet was obtained through centrifugation and washing of 1 ml of *Bifidobacterium breve* JKL2022 culture obtained through enrichment culture in mMRS medium. The microbial whole cell pellet was suspended in a reaction buffer to which LA was added at a concentration of 1.0 mg/ml, and the conversion rate (%) of LA to CLA was confirmed under the conditions of CLA production using cells (pH 7.0, reaction temperature 30° C., reaction time 30 minutes).

As shown in FIGS. 5A-5D, CLA production and conversion rate of the strain according to the concentration of LA were investigated while fixing the cell concentration and increasing the amount of LA added. It was confirmed that CLA was produced at a conversion rate of almost 100% within 30 minutes even when the concentration of LA in the reaction solution was increased to 5 mg/ml, and the conversion rate of 70% (7 mg/ml CLA) at a concentration of LA of 10 mg/ml.

FIG. 6 shows the CLA production characteristics when the concentration of cells was increased by 5 times and the concentration of LA as a substrate was 25 mg/ml. Even under these conditions, it was confirmed that almost all LA could be converted to CLA in one hour of reaction.

Considering that the upper limit LA concentration of 0.5 mg/ml was due to the antiproliferative effect of LA bacteria in fermentation process, it can be said that the superiority of whole cell biocatalysts is recognized.

The production of CLA using *Bifidobacterium breve* JKL2022 cells was about 79 times higher than that obtained through the culture process of *Bifidobacterium breve* JKL2022 strain. The fact that the reaction using bacterial cells takes only 1 hour, while the production of CLA through culture takes 24 hours, that is a big advantage.

<4-2> Characteristics of *Bifidobacterium breve* JKL2022 Strain

As shown in FIG. 4, when microbial cells were used as a whole-cell biocatalyst, the production of CLA was confirmed to be a characteristic of only *Bifidobacterium breve* JKL2022 strain of the present invention. It was found that other strains (FIG. 1) showing the ability to produce CLA by strain culture did not have such characteristics.

<4-3> Confirmation of Optimal Conditions for CLA Production by *Bifidobacterium breve* JKL2022 Cells 1) Optimal pH Condition As shown in FIG. 7, the optimal pH condition for CLA production using the cells of the strain was confirmed to be pH 9.0.

Example 5: Characteristics of CLA Production Using *Bifidobacterium breve* JKL2022 Cell-Free Extract <5-1> Preparation of Cell-Free Extract of Disrupted Microbial Strain For the production of CLA, *Bifidobacterium breve* JKL2022 strain (KACC 81214BP) was inoculated into MRS medium (mMRS; Sigma) containing 0.05% L-cysteine HCl and activated through two rounds of subculture at 37° C. for 18 hours under anaerobic conditions where 02 was replaced with $CO_2$. The activated strain was inoculated into a new mMRS medium (200 ml) and cultured at 37° C. for 24 hours under anaerobic conditions to obtain a strain. The culture solution of the strain was centrifuged at 10,000 rpm for 10 minutes at 4° C. The supernatant, which is a medium component, was recovered to prepare a cell-free extract (CFE) for CLA production and cells collected on the bottom were recovered and washed with PBS (phosphate buffered saline) three times.

The collected and washed cells were dispersed again in a PBS solution, and the cells were disrupted using an ultrasound sonicator (4 s operation, 10 s stop pattern, AMP 45% for 10 minutes). All these processes were performed at 4° C. using ice water to prevent enzyme inactivation due to overheating. The disintegrated strain was centrifuged at 12,000 rpm for 15 minutes at 4° C., and the supernatant was recovered to prepare a cell-free extract (CFE), which was used as a crude enzyme solution for CLA production. The production of CLA using CFE was carried out under similar reaction conditions as the production of CLA using the cells in Example 2.

<5-2> Optimal Conditions for CLA Production Using Cell-Free Extract

To compare the CLA production ability using CFE of *Bifidobacterium breve* strains prepared by the method of <5-1>, 12.5 μl/ml of CFE prepared through strain disruption and 1.0 mg/ml of LA, a substrate, were mixed and the ability of the strains to convert LA to CLA was compared.

As shown in FIG. 8, the ability to produce CLA using CFE under the condition of pH 6.5 and temperature 35° C. was confirmed to be a characteristic of *Bifidobacterium breve* JKL2022 strain of the present invention.

1) pH Condition

The optimal pH and optimal temperature conditions for CLA production using CFE of the strain were confirmed. As shown in FIG. 9, the optimal pH for CLA production using CFE of the strain was 5 to 8, preferably 5.5 to 7, and more preferably 6.5.

2) Temperature Condition

The optimal pH and optimal temperature conditions for CLA production using CFE of the strain were confirmed. As a result, as shown in FIG. 10, it was confirmed that the optimal temperature for CLA production using CFE of the strain was 20 to 50° C., preferably 30 to 45° C., and more preferably 40° C.

The production of CLA by CFE of *Bifidobacterium breve* JKL2022 strain according to the present invention was confirmed with a CLA conversion rate of 46% when LA, a substrate, was used at a concentration of 1.0 mg/ml. Compared to other comparative strains with a CLA conversion rate of less than 3%, the most CLA was produced when CFE of *Bifidobacterium breve* JKL2022 strain of the present invention was used (FIG. 8).

Accession Number

Depositary Authority: Korean Agricultural Culture Collection, National Institute of Agricultural Sciences Address of depository institution: 370, Nongsaengmyeong-ro, Iseo-myeon, Wanju-gun, Jeollabuk-do 55365, Republic of Korea.

Deposit Number: Accession Number: KACC 81214BP

Deposit Date: May 11, 2022

The invention claimed is:

1. A method for converting linoleic acid (LA) to conjugated linoleic acid (CLA) comprising the following steps:

1) a step of obtaining cells of *Bifidobacterium breve* JKL2022 strain deposited as KACC81214BP; and 2) a step of contacting the cells obtained in step 1) with a reaction buffer containing LA to convert the LA to CLA.

2. A method for converting linoleic acid (LA) to conjugated linoleic acid (CLA) comprising the following steps:

1) a step of obtaining cells of *Bifidobacterium breve* JKL2022 strain deposited as KACC81214BP;

2) a step of obtaining a cell-free extract of *Bifidobacterium breve* JKL2022 strain deposited as KACC81214BP by crushing the cells obtained in step 1); and 3) a step of contacting the cell free extract obtained in step 2) with a reaction buffer containing LA to convert the LA to CLA.

3. The method for converting LA to CLA according to claim 1, wherein the CLA is characterized by including a conjugated double bond at the cis-9/trans-11 position.

4. The method for converting LA to CLA according to claim 1, wherein the reaction buffer has a pH of 7 to 10.

5. The method for converting LA to CLA according to claim 2, wherein the reaction buffer has a pH of 5 to 7.5.

6. The method for converting LA to CLA according to claim 2, wherein the CLA is characterized by including a conjugated double bond at the cis-9/trans-11 position.

* * * * *